United States Patent [19]
Jones et al.

[11] Patent Number: 5,814,343
[45] Date of Patent: Sep. 29, 1998

[54] COSMETIC COMPOSITION

[75] Inventors: Malcolm N Jones, Cheshire; Michael Kaszuba, Merseyside; Ian G Lyle, Deeside, all of United Kingdom

[73] Assignee: Unilever Patent Holding B.V., Vlaardingen, Netherlands

[21] Appl. No.: 604,647

[22] Filed: Feb. 21, 1996

Related U.S. Application Data

[62] Division of Ser. No. 46,856, Apr. 15, 1993, Pat. No. 5,510,120.

[30] Foreign Application Priority Data

Apr. 15, 1992 [GB] United Kingdom .................. 9208339

[51] Int. Cl.$^6$ .............................. A61K 7/48; A61K 7/06; A61K 9/50; A61K 9/127
[52] U.S. Cl. ...................... 424/499; 424/70.1; 424/401; 424/450
[58] Field of Search .................... 424/401, 450, 424/500, 499; 436/528, 829; 428/402.2, 402.24; 450/489; 514/844

[56] References Cited

U.S. PATENT DOCUMENTS

| | | | |
|---|---|---|---|
| 3,987,161 | 10/1976 | Widder | 424/70 |
| 4,429,008 | 1/1984 | Martin et al. | 428/402.2 |
| 4,508,703 | 4/1985 | Redziniak | 424/38 |
| 4,944,948 | 7/1990 | Uster et al. | 424/450 |
| 5,064,655 | 11/1991 | Uster et al. | 424/450 |
| 5,128,139 | 7/1992 | Brown et al. | 424/450 |
| 5,137,725 | 8/1992 | Handjani et al. | 424/401 |
| 5,153,000 | 10/1992 | Chikawa et al. | 424/450 |
| 5,169,631 | 12/1992 | Rase et al. | 424/401 |
| 5,173,303 | 12/1992 | Lau et al. | 424/450 |
| 5,248,590 | 9/1993 | Rutner et al. | 435/5 |
| 5,286,629 | 2/1994 | Denis et al. | 435/71 |
| 5,401,511 | 3/1995 | Margalit | 424/450 |
| 5,411,730 | 5/1995 | Kirpostin et al. | 424/322 |
| 5,462,751 | 10/1995 | Kossovsky et al. | 424/494 |
| 5,510,120 | 4/1996 | Jones et al. | 424/70.1 |
| 5,603,872 | 2/1997 | Margalit | 264/4.3 |

FOREIGN PATENT DOCUMENTS

| | | | |
|---|---|---|---|
| 38724/89 | 2/1990 | Australia | C12N 9/10 |
| 80218 | 1/1992 | Australia . | |
| 12592/92 | 9/1992 | Australia | A61K 9/127 |
| 13677/92 | 9/1992 | Australia | A61K 9/127 |
| 78979/91 | 12/1992 | Australia | A61K 9/127 |
| 25956/92 | 5/1993 | Australia | A61K 7/00 |
| 33939/93 | 5/1993 | Australia | A61K 9/127 |
| 0423002 | 4/1991 | European Pat. Off. . | |
| 0481701 | 4/1992 | European Pat. Off. . | |
| 0120722 | 10/1984 | France . | |
| 2597345 | 10/1987 | France . | |
| 0429912 | 1/1992 | Japan . | |
| 0441413 | 2/1992 | Japan . | |
| 9011069 | 3/1990 | WIPO . | |
| 9009782 | 9/1990 | WIPO . | |
| 9014096 | 11/1990 | WIPO . | |
| 9119501 | 12/1991 | WIPO . | |
| 9300076 | 7/1993 | WIPO . | |

OTHER PUBLICATIONS

Cerdan et al, "Human Keratinocyte Membrane Lectins: Characterization and Modulation of Their Expression by by Cytokines", Biol. Cell, 1991, vol. 73, pp. 35–42.

*Primary Examiner*—Stephanie W. Zitomer
*Attorney, Agent, or Firm*—Pillsbury, Madison & Sutro LLP Cushman Darby & Cushman IP Group

[57] ABSTRACT

A cosmetic composition for topical application to the skin and/or hair includes, optionally in a cosmetically or pharmaceutically acceptable vehicle, particles which enclose a cosmetically-effective benefit agent active at a target location accessible by application to the skin and/or hair, and which have means to bind to an organic surface at the target location. In particular, the particles are liposomes and have means for binding to microorganisms present on the skin and/or hair, for example those responsible for skin disorders, scalp irritation, and underarm and foot odour.

11 Claims, No Drawings

COSMETIC COMPOSITION

This is a division of application Ser. No. 08/046,856, filed Apr. 15, 1993, now U.S. Pat. No. 5,510,120.

FIELD OF THE INVENTION

This invention relates to a cosmetic composition to be used for the delivery of a cosmetically-effective benefit agent to a target site on the skin and/or hair. In particular the invention relates to a cosmetic composition in which the benefit agent is included in a particle by means of which it is delivered to its target site.

BACKGROUND OF THE INVENTION

It has become common practice in recent years for cosmetic formulations such as skin creams to contain liposomes. Liposomes are small sacs formed from certain surface active molecules, most commonly phospholipids, which in aqueous media arrange themselves into a bi-layered membrane defining a microscopic closed vesicle. Liposomes are commonly employed in moisturising creams because they enhance the delivery of water to the skin.

It is also known to deliver therapeutic agents to the skin in microcapsules, in particular by encapsulating the therapeutic agent in liposomes. For example, EP-A-0224837 (Rohm Pharma GmbH) discloses compositions for treating skin disorders in which the active ingredient is encapsulated in liposomes comprising lecithin and cholesterol. WO085/03640 (The Liposome Company, Inc.) discloses pharmaceutical formulations which may be topically applied and in which liposomes are held in a gel matrix to provide improved retention and sustained release of entrapped bioactive agents at the site of application.

It is also known to use liposomes to target therapeutic agents to target sites within the body. In general, a molecule which binds specifically at the target site is attached to the liposome to target the therapeutic agent to the appropriate site. For example, EP-A-036277 (Regents of the University of California) discloses a method for attaching to liposomes proteins, such as antibodies or antibody fragments, which bind specifically to a target site. In particular, the reference is concerned with targeting cytotoxic drugs to tumours in the body.

WO87/07150 (The John Hopkins University) discloses pharmaceutical compositions which comprise nanoparticles, of which liposomes are one example, which are targeted by means of surface site-directing molecules capable of binding cell receptors and which are, themselves, therapeutic or pharmacologic agents. Although the reference makes passing reference to topical application, it is primarily concerned with treating, or performing diagnosis on, diseased inner organs or tissues.

Similarly, W088/00824 contemplates targeting liposomes containing therapeutic agents to mucosal surfaces by means of positively charged groups at the surface of the liposomes.

The benefits which may be obtained by directing particles including cosmetically-effective benefit agents to target sites on the skin and/or the hair do not appear to have been appreciated to date.

SUMMARY OF THE INVENTION

According to a first aspect, the present invention provides a cosmetic composition for topical application to skin and/or hair comprising: particles, which include a cosmetically effective benefit agent, said particles having means to bind to an organic surface at a target location accessible on application of the composition to the skin and/or hair; and, optionally, a cosmetically acceptable vehicle.

In a second aspect, the invention provides a method of cosmetic treatment of the skin and/or hair comprising applying to the skin and/or hair a composition according to the first aspect.

In a still further aspect, the invention provides a method for the production of a cosmetic composition according to the first aspect, said method comprising:
  including a cosmetically effective benefit agent in particles;
  providing, at the surface of said particles means to bind an organic surface at a target location accessible on application of the composition to the skin and/or hair; and, optionally, admixing said particles and a cosmetically acceptable vehicle.

Cosmetic compositions for topical application to the skin or hair are typically of two kinds: "rinse-off" or "leave on". In the case of rinse-off compositions which, as their name suggests, are washed off shortly after their application, their benefit agents generally remain in contact with the skin or hair for short times only and this limits their effectiveness. By providing for binding of particles including a benefit agent at a particular target site one can ensure retention of the benefit agent at the site and prolonged delivery of the benefit agent. Greater selectivity may also be provided since any particles that are deposited at other than the target site and which are unable to bind where they are deposited can be easily washed away. The combination of site discrimination with binding at the site means that potentially noxious molecules may be used effectively at low concentrations. The present inventors have surprisingly found that a small amount of a cosmetically-effective benefit agent, when targeted to a particular site, in particles capable of binding to that site, can be rendered much more effective relative to the same concentration of benefit agent used in free solution, when each is applied for a realistically short contact time.

Analogous benefits may be achieved in cosmetic compositions which are to be left on the skin or hair. In conventional compositions after application, the concentration of the benefit agent at the site where its action is desired tends to decrease with time, for example as it is diluted through perspiration or with environmental moisture or when the hair or skin is, ultimately, washed. Binding of particles including a benefit agent at a particular target site where action of the benefit agent is desired, again may promote prolonged release of the benefit agent.

DETAILED DESCRIPTION OF THE INVENTION

The present invention relates, in a first aspect to a cosmetic composition. The term "cosmetic composition" should be understood to encompass compositions intended to enhance the appearance, or to inhibit or prevent a deterioration in appearance, of the body surface including the hair. However, the term is not limited to appearance-enhancing compositions, and encompasses also compositions intended to modify or enhance body odour as well as cleaning compositions which may produce no detectable change of appearance.

The term "cosmetically-effective benefit agent" should be similarly broadly understood and intends an agent which when included in a cosmetic composition in an appropriate amount is intended to produce a cosmetic benefit.

The particles included in compositions of the first aspect may be microparticles or nanoparticles, for example made of synthetic polymeric substances such as polycyanoacrylate, polyanhydrides of aromatic and aliphatic dicarboxylic acids, polymethylcyanoacrylate and the like. They may also be formed of proteins such as albumin and gelatin. Examples of the formation of such particles may be found in "Polymeric Nanoparticles and Microspores", Boca Raton, CRC Press (1986). The cosmetically effective benefit agent may be entrapped in, or adsorbed onto, or into the particles.

The preferred particles for inclusion in the composition of the first aspect are, however, liposomes.

Liposomes may be prepared from those surface active materials which are known for the purpose; examples are given in JH Fendler, "Membrane Mimetic Chemistry" (Wiley-Interscience, New York, 1982) and in JN Weinstein and JD Leserman, Pharmac, Ther., 1984 24, 207–233. Among the materials most commonly used are phospholipids from natural sources such as lecithin from egg or soya, and synthetic analogues such as L-α-dipalmitoyl phosphatidylcholine (DPPC). Charged phospholipids such as phosphatidyl serine are often incorporated in liposomes to improve colloidal stability.

Techniques for preparation of liposomes are described in G Gregoriadis, "Liposome Technology—Vol 1", (CRC Press, 1984) and in PR Cullis et al., "Liposomes—from Biophysics to Therapeutics", Chapter 5, (Ed. MJ Ostro, Marcel Dekker, New York, 1987). Possible methods include sonication (in an ultrasonic bath) of a phospholipid dispersion and reverse phase evaporation. Another method which may be used is "extrusion" under pressure through very fine passages such as provided by polycarbonate membranes, such as Nuclepore™ or Poretics™ membranes.

The techniques lead to somewhat different liposomes. Sonication and extrusion generally lead to small vesicles, less than 200 nm in diameter. Reverse phase evaporation leads to larger vesicles having diameters ranging from 100 nm up to several microns.

Liposomes may act as carriers for water-soluble, oil-soluble or microcrystalline solid benefit agents. Incorporation of a water-soluble benefit agent into liposomes may be accomplished by including the material in the aqueous solution during liposome formation. When the liposomes are formed, some of the solution becomes enclosed within the vesicles. Oil-soluble benefit agents may be incorporated by including the material in the lipid mixture prior to formation of the liposomes; such agents are normally then sequestered in the lipid membrane. Microcrystalline solid benefit agents may be incorporated for example by internal precipitation of insoluble salts when one of the constituent ions is encapsulated and the other is allowed to permeate through the liposomal membrane from the external solution.

Preferably, the means for binding the organic surface is specific for the organic surface at the selected target location on the skin and hair and does not effect binding to organic surfaces at other target sites accessible by topical application. For example the means for binding may be, a molecule which binds specifically to a microorganism present at the target site. Means for attaching particles of the cosmetic composition to a target are suitably provided at the exterior of the particles and may be selected from molecules having strong affinity for a surface at said target. For example, suitable molecules, especially when the particles are liposomes include specifically binding proteins, polysaccharides, glycoproteins, phospholipids, glycolipids, lipoproteins or lipopolysaccharide.

One such type of molecule is an antibody, which might be monoclonal or polyclonal. Monoclonal antibodies may be generated using the technique first described by Kohler and Milstein (Nature, 256, 495–479, 1975). Antibodies may, alternatively be generated by the use of recombinant DNA techniques, for example as described in U.S. Pat. Nos. 4,816,397 and 4,816,567. Specific binding subunits or antibody fragments may also be used. These may be generated by enzymic digestion of intact antibody molecules, for example using papain or pepsin, or may be produced using the recombinant DNA techniques described in the two US patents referred to above.

A further possibility is to use a lectin bound to the outer surface of the particles e.g. liposomes. Lectins are proteins with binding affinity for certain sugar groups which occur in polysaccharides and glycoproteins. Their binding affinity tends to be less specific than that of antibodies. Examples include wheat germ agglutinin (WGA) and concanavalin A(ConA).

Both antibodies and lectins can be bound to liposomes by covalent bonds. Various techniques are known for conjugating proteins to other materials and generally entail providing each of the two species with one of a pair of materials which will react together. Suitable methods are described in MJ Ostro, "Liposomes—from Biophysics to Therapeutics", Chapter 5 (Marcel Dekker, New York, 1987) and in F J Martin et al., "Liposomes—A Practical Approach", Chapter 4 (Ed R R C New, IRL Press, Oxford, 1990). Our preferred technique for attaching to liposomes is to react m-maleimidobenzoyl-N-hydroxysuccinimide (MBS) with a component of the phospholipid mixture before formation of the liposomes and to react N-succinimidyl-S-acetylthioacetate (SATA) with the protein. After liposome formation the SATA derivative of the protein is deacetylated with hydroxylamine and coupled to the liposome in aqueous medium under mild conditions.

The use of these materials to conjugate antibodies and lectins to liposomes has been described in F. J. Hutchinson et al., Biochim. Biophys. Acta., 978 (1989) 17–24.

The inventors have found that inclusion in a liposome of a binding means selected from molecules having a hydrophobic tail and a more hydrophilic alcohol or sugar headgroup, for example a glycolipid or phospholipid with a sugar or polyhydric alcohol headgroup, may also be used to effect binding of liposome to organic surfaces at target locations on the hair and skin. Preferred targeting molecules of this type have alcohol or sugar head groups bearing 2 to 10, preferably 2 to 6, hydroxyl groups. Examples of such molecules include phosphatidyl inositols which have pentahydric alcohol head groups, phosphatidyl glycerols and cerebrosides. The inventors have found that when such molecules are included in liposomes in a sufficient quantity, they promote binding of the liposomes to microorganisms which are typically present on the skin. The amount of such glycolipids or phospholipids included in the liposome to promote binding depends on the particular compound included, as well as on the nature of other surface active molecules included in the liposome. In some cases, the surface active molecules of the liposome may consist entirely of one or more glycolipids and/or one or more phospholipids having a sugar or polyhydric alcohol head group. Alternatively, such compounds may constitute a fraction only of the total surface active molecules. For example, such glycolipids and/or phospholipids may be included in the mixture of surface active molecules which form the liposomes in an amount of at least 6 mole %, preferably not more than 18%, desirably not more than around 16%. This is particularly so where the liposome includes phosphatidyl inositol as targeting agent and phosphatidyl choline. A particularly preferred range is from 8 to 14 mole % of such glycolipids and/or phospholipids.

In preferred embodiments of the invention, target locations include skin and hair themselves, hair follicles, sweat ducts, scalp, feet, underarm area, pimples and other skin lesions.

The particles may be provided with binding means such that they have affinity for an organic material such as a proteoglycan, protein, glycoprotein or carbohydrate exposed at the target site. In particular, it is desirable that the particles have means to bind microorganisms which may be present at the target location. Examples of such microorganisms include those of the genera Pityrosporum, Mallassezia, Coryneform, Propionibacterium, Micrococcus, Staphylococcus, Proteus and Trichophyton. Specific examples are: *Pityrosporum ovate* and *Malassezia furfur* and other microorganisms which occur in the hair or on the scalp, Coryneform bacteria and other microorganisms typically present in the underarm area; *Propionibacterium acnes, Micrococcus species, Staphylococcus aureus* and other microogranisms present on, and responsible for lesions of, the skin; and *Staphylococcus epidermidis, Proteus vulgaris* and *Trichophyton mentagrophytes* and other microorganisms typically present on the feet.

Benefit agents which may be employed in the compositions and methods of the invention include one or more of antimicrobials, anti-inflammatory agents, perfumes, antiperspirants, deodorants, sunscreens, antioxidants, hair growth agents, moisturising agents, cleansing agents and conditioning agents. It is preferred that the benefit agent be an antimicrobial. Examples include antibacterial agents having a molecular weight not greater than 2000. Within this category, biphenolic compounds are of interest, a preferred example being Triclosan (2,4,4'-trichloro-2'-hydroxy diphenyl ether) which is a broad spectrum antibacterial agent. Other antimicrobials include chlorhexidine, zinc pyrithione, farnesol, triethyl citrate, benzoic acid, benzyl benzoate, ethyl lactate, undecelenic acid, benzethonium chloride, and metal salts containing $Zn^2+$, $Cu^2+$ or $Ag+$ and quaternary ammonium surfactants such as cetyl trimethyl ammonium bromide.

The compositions of the first aspect preferably include a vehicle, such as a cosmetically acceptable vehicle, to act as a dilutant, dispersant or carrier for the particles so as to facilitate distribution of the particles at the site of application of the composition. The particular choice of vehicle will depend on the method chosen for administration as well as on the site to which the composition is applied.

Vehicles can include water or substances such as liquid or solid emollients, solvents, humectants, thickeners and powders. Examples of each of these types of vehicle, which can be used singly or as mixtures of one or more vehicles, are as follows:

Emollients, such as stearyl alcohol, glyceryl monoricinoleate, glyceryl monostearate, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, eicosanyl alcohol, behenyl alcohol, cetyl palmitate, silicone oils such as dimethylpolysiloxane, di-n-butyl sebacate, isopropyl myristate, isopropyl palmitate, isopropyl stearate, butyl stearate, polyethylene glycol, triethylene glycol, lanolin, cocoa butter, corn oil, cotton seed oil, tallow, lard, olive oil, palm kernel oil, rapeseed oil, safflower seed oil, evening primrose oil, soybean oil, sunflower seed oil, avocado oil, sesame seed oil, coconut oil, arachis oil, castor oil, acetylated lanolin alcohols, petroleum jelly, mineral oil, butyl myristate, isostearic acid, palmitic acid, isopropyl linoleate, lauryl lactate, myristyl lactate, decyl oleate, myristyl myristate;

Propellants, such as trichlorofluoromethane, dichlorodifluoromethane, dichlorotetrafluroethane, monochlorodifluoromethane, trichlorotrifluoroethane, propane, butane, isobutane, dimethyl ether, carbon dioxide, nitrous oxide;

Solvents, such as ethyl alcohol, methylene chloride, isopropanol, acetone, ethylene glycol monoethyl ether, diethylene glycol monobutyl ether, diethylene glycol monoethyl ether, dimethyl sulphoxide, dimethyl formamide, tetrahydrofuran;

Humectants, such as glycerin, sorbitol, sodium 2-pyrrolidone-5-carboxylate, soluble collagen, dibutyl phthalate and gelatin;

Powders, such as chalk, talc, fullers earth, kaolin, starch, gums, colloidal silica, sodium polyacrylate, tetra alkyl and/or trialkyl aryl ammonium smectites, chemically modified magnesium aluminium silicate, organically modified montmorillonite clay, hydrated aluminium silicate, fumed silica, carboxyvinyl polymer, sodium carboxymethyl cellulose, ethylene glycol monostearate.

The cosmetically acceptable vehicle will usually form from 10 to 99.9%, preferably from 50 to 99% by weight of the composition, and can, in the absence of other cosmetic adjuncts, form the balance of the composition.

The composition according to the invention can also comprise other materials which are conventionally useful in cosmetic or therapeutic products for topical application to skin and hair. Examples include surfactants, especially anionic, nonionic and amphoteric surfactants, polymers such as Polymer JR and Jaguar gums, preservatives, perfumes, moisturisers, antioxidants, etc.

The compositions of the invention can be formulated as liquids, for example as a lotion, shampoo, milk or cream for use in conjunction with an applicator such as a roll-ball applicator, or a spray device such as an aerosol can containing propellant, or a container fitted with a pump to dispense the liquid product.

Alternatively, the compositions of the invention can be solid or semi-solid, for example sticks, creams or gels, for use in conjunction with a suitable applicator or simply a tube, bottle or lidded jar, or as a liquid-impregnated fabric, such as a tissue wipe.

The invention accordingly also provides a closed container containing a composition as herein defined.

The proportion of benefit agent in the particles may vary widely. The benefit agent will generally provide from 0.0005% to 50% by weight of the particles which in turn will generally provide from 0.01 to 50% especially 0.1 to 50% by weight of the composition. The benefit agent will generally provide from 0.00002 to 10% by weight of the composition.

The benefit agent preferably provides from 0.001 to 30%, more especially 0.005 to 10% by weight of the particles. The particles will preferably constitute 0.1 to 10% more especially 1 to 5% by weight of the composition. The benefit agent preferably provides from 0.00005 to 5%, better 0.0001 to 1% by weight of the overall composition.

EXAMPLES

Embodiments of the invention are described below by way of example only.

Example 1: Targeting of liposomes to Staphylococcus epidermidis

Liposome preparation (a) With phosphatidyl inositol (PI) as targeting molecule: 27 mg of dipalmitoyl phosphatidyl choline (DPPC, radio labelled with $^3$H-DPPC) and 1 mg of phosphatidyl inositol (PI, from wheat germ) were dissolved in 9 ml chloroform/methanol (4:1 v/v mixture) and the solution placed in a round bottomed flask. The solvent was removed by rotary evaporation (60° C.) to leave a thin lipid film. This was hydrated and redispersed by shaking with 3 ml of phosphate buffered saline (PBS) at 60° C. The resulting multilamellar vesicles (MLV's) were subjected to several freeze-thaw cycles before extruding 10 times, at 60° C. and under nitrogen pressure, through a Poretics 0.1 μm polycarbonate filter held in a Lipex Biomembranes Extruder (10 ml barrel). This procedure generated a fairly monodisperse population of vesicles (VET's) which were sized by photon correlation spectroscopy, following the method described in Hutchinson et al., Biochim, Biophys. Acta, 978 (1989), 17–24.

The amount of PI included in the preparation was varied between 1 and 8 mg (Samples A to E in Table 1) to examine the effects of changing surface density of site directing molecules on targeting efficiency.

For comparison of untargeted vesicles, the PI was replaced in some preparations by phosphatidyl serine (PS), a negatively charged phospholipid which maintains the colloidal stability of the vesicular suspension but which lacks the multiple bonding potential of the inositol headgroup (Examples F and G in Table 1).

(b) With the lectin wheat germ agglutinin (WGA) as targeting molecule: The preferred technique for attaching lectins to liposomes is to use covalent coupling agents. m-Maleimidobenzoyl-N-hydroxysuccinimide (MBS) is reacted with the phospholipid dipalmitoyl phosphatidyl ethanolamine (DPPE) and the product, DPPE-MBS, is included in the phospholipid mixture before formation of the liposomes. The protein (WGA) is reacted with N-succinimidyl-S-acetylthioacetate (SATA) to yield a thiolated derivative which can then be coupled to the preformed liposomes, in aqueous medium under mild conditions, via the DPPE-MBS.

The DPPE-MBS may be prepared as follows: 40mg L-α-dipalmitoylphosphatidylethanolamine (DPPE) is dissolved in a mixture of 16 ml dry chloroform, 2 ml dry methanol and 20 mg dry triethylamine. 20 mg maleimidobenzoyl-N-hydroxysuccinimide ester (MBS) is added and the reaction mixture is stirred under nitrogen at room temperature for 24 h, after which the organic phase is washed three times with phosphate buffered saline (PBS pH7.3) to remove unreacted MBS. The DPPE-MBS derivative is recovered from the organic phase by rotary evaporation and stored in a chloroform/methanol mixture (9:1 v/v) at 4° C.

The derivatisation of WGA with SATA may be carried out as follows:

2.5 µl of a stock solution containing 9.08 mg N-succinimidyl-S-acetyl thioacetate (SATA) in 50 µl dimethylformamide is added to WGA solution (10 mg in 2.5 ml phosphate (5 mM)—EDTA (1 mM) buffer, pH7.5) at room temperature. After reaction (15 min) the derivatised protein (s-WGA) is separated from unreacted SATA by gel filtration on a Sephadex G-50 column (15×2 cm). The s-WGA is activated by deacetylation using, for each 2 ml of protein solution, 200 µl of 0.1M hydroxylamine solution, made up in 2.5 mM EDTA with sufficient solid $Na_2HPO_4$ added to bring the pH to 7.5.

The preparation of liposomes incorporating the DPPE-MBS is as described in (a) above. Conjugation of the derivatised protein to the liposomes was accomplished simply by mixing and equilibrating aliquots of the dispersion with the deacetylated SATA derivative of WGA in appropriate proportions at room temperature for 2 hours or at 4° C. overnight. After conjugation the product was passed through a Sepharose 4B gel filtration column to separate the proteoliposomes from unreacted protein.

Targeting assay

*Staph. epidermidis* was used in this example as an example of the microorganisms which may be present on, and cause malodour of feet. The ability of vesicles carrying surface PI or lectin to target to *Staph. epidermidis* was measured by equilibration of the radiolabelled vesicles with a layer of the bacteria grown in the wells of a standard polystyrene microtitre plate, followed by washing, resuspension and measurement of the bound $^3$H-DPPC.

*Staph. epidermidis* was grown aerobically for 18 h at 37° C. in a medium containing 10% BHI and 0.3% yeast extract. The bacteria were harvested by centrifugation (2000 rpm, 5 min), washed 3 times with sterile PBS and resuspended in PBS to give an optical density at 550 nm of 0.5 200 µl of suspension was pipetted into each well of a microtitre plate and was left overnight to adsorb. After incubation the well was washed twice with 300 µl sterile PBS and the plate was blotted dry.

200 µl of test solution containing vesicles with or without targeting molecules was added to the well and left for 2 hours at 370° C. to absorb.

Results

The results of the targeting assay with PI as the targeting molecule are summarised in Table 1. The last column of the table shows the percentage targeting relative to total coverage rather than to the amount of lipid added to the plates. It can be seen from this that the extent of binding of VET's to the bacterial film is a sensitive function of the mole % of PI in the vesicles, reaching a maximum at about 11.4%. The level of attachment of vesicles without PI, or with much more or less PI, is very low.

The results of the targeting assay with WGA as the targeting species are summarised in Table 2. In this case, the level of PI was kept constant at 1mg in the preparation —enough of the charged lipid to maintain colloidal stability of the vesicular suspension but not enough to provide effective targeting to *Staph. epidermidis*. The lectin in this case improves targeting efficiency by a factor of 4, although at the levels of WGA studied this was not as great as with PI alone at its optimum level.

Example 2: Targeting of liposomes to Proteus vulgaris.

Preparation of liposomes

Liposomes containing phosphatidyl inositol as targeting molecule were prepared as described above at Example 1(a). *Proteus vulgaris* is another microorganism which may be present on the feet.

Targeting assay

This was also carried out as described above in Example 1 except that Proteus vulgaris was used in place of *Staph. ePidermidis*.

Results

The results of the assay with PI as the targeting molecule are summarised in Table 3. The efficiency of delivery and retention on a film of *Proteus vulgaris* is again a function of the level of PI in the vesicles. Unlike *Staph. epidermidis*, however, there are two ratios of PI:DPPC within the range studied at which targeting shows maxima. This suggests a complex interplay of effects such as electrostatic repulsion, hydrogen bonding between PI and surface carbohydrates of the microbial cell wall, and "patching" of the PI within the vesicular membrane itself.

Example 3: Targeting of liposomes to Coryneform hofmanni

Preparation of liposomes

Liposomes having phosphatidyl inositol as targeting molecule were prepared as described in Example 1. Alternatively, the lectin Con A was used as targeting molecule. In that case, liposomes were prepared as in Example 1 for WGA, except that succinylated Con A (sConA) was purchased directly (available from Sigma).

Targeting Assay

This was carried out as described in Example 1 except that *Coryneform hofmanni* was used instead of *Staph. epidermi-*

*dis.* Microorganisms of genus Coryneform are commonly found in the underarm area.

Results

The results of targeting assays using ConA as the targeting molecule are summarised in Table 4. These experiments were done at a constant level of PI in the vesicles of 8.8 mole %. In the absence of ConA, the delivery was only 8.5%. With the lectin expressed on the surface of the vesicles, targeting was markedly improved, although it did not reach the high levels observed previously for PI vesicles with *Staph. epidermidis* or *Proteus vulgaris*.

Example 4

The targeting assay of Example 1 was repeated using diphosphatidyl glycerol (DPPG) as targeting molecule rather than phosphatidyl inositol. The results, shown in Table 5, indicate that optimum apparent monolayer coverage was obtained for around 6 to 7 mole % DPPG in DPPC.

Example 5

Assessment of Efficacy (I)

The antibacterial efficacy of Triclosan delivered in targeted liposomes was assessed using a bacterial regrowth assay.

Liposomes containing Triclosan were prepared as described above in Example 1(a) except that dipalmitoyl phosphatidyl glycerol (DPPG) was used in place of DPPC and Triclosan (6 µg for 31 mg lipid) was added to the chloroform/methanol mixture employed in the first step of liposome formation. Phosphatidyl inositol was used as targeting molecule. Liposome fractions following gel filtration were analysed for phospholipid [$^{14}$C-DPPC] and Triclosan [$^{3}$H-tritiated] by scintillation counting. Particle size was determined and fractions having two different mean diameters were selected for use in the assay.

In order to perform the regrowth assay, the bacterium *Staph. epidermidis* was grown for 18 h at 37° C. in medium containing 10% BHI, 0.3% yeast extract. The bacteria were harvested by centrifugation (2000 rpm, 5 min), washed 3 times with sterile PBS and resuspended in PBS to give an optical density at 550 nm of 0.5. 200µl of suspension was pipetted into a microtitre plate well and left overnight to adsorb. After incubation the well was washed twice with 300 µl sterile PBS, and the plate was blotted dry. Non-specific binding sites were then blocked by treatment for 30 min at 20° C. with a sterile solution of 0.02% w/v casein in PBS, after which the well was washed 3 times with PBS and the plate blotted dry.

200 µl of test solution containing either liposomes with Triclosan, or an equivalent amount of free Triclosan all in PBS containing 10% ethanol (Triclosan is virtually insoluble in PBS alone; this level of ethanol does not kill the bacteria), was added to the well and allowed to adsorb for 2 minutes at 37° C. The plate was then washed 3 times with sterile PBS, 200 µl growth medium added (10% BHI plus 0.3% yeast extract) sealed and incubated for 18 h at 37° C. After this incubation period, the plate was read using a Dynatech MR610 plate reader and the extent of continuing bacterial growth determined from the measured optical density at 630 nm.

The results are set out in Table 6 and indicate that a higher percentage kill could be achieved with PI targeted liposomes than with an equivalent amount of free Triclosan.

Example 6

Assessment of Efficacy (II)

Example 5 was repeated with liposomes of DPPC containing phosphatidyl inositol as targeting agent. The results shown in Table 7A and 7B indicate the improved efficacy of killing which may be achieved by targeting liposomes with PI.

TABLE 1

*STAPHYLOCOCCUS EPIDERMIDIS*
(TARGETTED WITH PHOSPHATIDYL INOSITOL)

| VET Sample | COMPOSITION (mg) | | | $d_w$ (nm) | Moles Lipid Per ml |
|---|---|---|---|---|---|
| | DPPC | PI | PS | | |
| (A) | 27 | 1 | 0 | 77.38 | $3.79 \times 10^{-6}$ |
| (B) | 27 | 2 | 0 | 87.57 | $3.91 \times 10^{-6}$ |
| (C) | 27 | 3 | 0 | 76.14 | $4.03 \times 10^{-6}$ |
| (D) | 27 | 4 | 0 | 71.85 | $4.14 \times 10^{-6}$ |
| (E) | 27 | 5 | 0 | 86.08 | $4.26 \times 10^{-6}$ |
| (F) | 27 | 0 | 3 | 102.1 | |
| (G) | 27 | 0 | 6 | 103.1 | |

| | $d_w$ | Projected Area m$^2$ | No. of liposomes at monolayer coverage | Moles lipid added to plate | Moles lipid adsorbed to plate | No. of adsorbed vesicles | % Targeted vesicles |
|---|---|---|---|---|---|---|---|
| (A) | 77.38 | $4.70 \times 10^{-15}$ | $4.69 \times 10^{10}$ | $7.58 \times 10^{-7}$ | $1.59 \times 10^{-10}$ | $1.54 \times 10^{9}$ | 3.29 |
| (B) | 87.57 | $6.02 \times 10^{-15}$ | $3.66 \times 10^{10}$ | $7.82 \times 10^{-7}$ | $2.91 \times 10^{-10}$ | $2.15 \times 10^{9}$ | 5.88 |
| (C) | 76.14 | $4.55 \times 10^{-15}$ | $4.84 \times 10^{10}$ | $8.06 \times 10^{-7}$ | $7.88 \times 10^{-10}$ | $7.92 \times 10^{9}$ | 16.36 |
| (D) | 71.85 | $4.06 \times 10^{-15}$ | $5.43 \times 10^{10}$ | $8.28 \times 10^{-7}$ | $3.70 \times 10^{-9}$ | $4.23 \times 10^{10}$ | 77.90 |
| (E) | 86.08 | $5.82 \times 10^{-15}$ | $3.78 \times 10^{10}$ | $8.52 \times 10^{-7}$ | $6.55 \times 10^{-10}$ | $5.04 \times 10^{9}$ | 13.30 |
| (F) | 102.1 | | | | | | 4.24 |
| (G) | 103.1 | | | | | | 4.89 |

Note:
$d_w$ = vesicle diameter as measured by photocorrelation spectroscopy

TABLE 2

STAPHYLOCOCCUS EPIDERMIDIS
(with WGA)

| VET Sample | COMPOSITION (mg) | | | $d_w$ (nm) | $P_w$ | Moles Lipid per ml |
|---|---|---|---|---|---|---|
| | DPPC | PI | DPPE-MBS | | | |
| (H) | 27 | 1 | 0 | 77.38 | 0 | $3.79 \times 10^{-6}$ |
| (I) | 27 | 1 | 3 | 89.61 | 10.75 | $4.52 \times 10^{-6}$ |
| (J) | 27 | 1 | 3 | 88.62 | 16.42 | $2.41 \times 10^{-6}$ |

| | $d_w$ | Projected Area m$^2$ | No. of liposomes at monolayer coverage | Moles lipid added to plate | Moles lipid adsorbed to plate | No. of adsorbed vesicles | % Targeted vesicles |
|---|---|---|---|---|---|---|---|
| (H) | 77.38 | $4.70 \times 10^{-15}$ | $4.69 \times 10^{10}$ | $7.58 \times 10^{-7}$ | $1.11 \times 10^{-10}$ | $1.08 \times 10^{9}$ | 2.29 |
| (I) | 89.61 | $6.31 \times 10^{-15}$ | $3.49 \times 10^{10}$ | $9.04 \times 10^{-7}$ | $4.46 \times 10^{-10}$ | $3.14 \times 10^{9}$ | 8.99 |
| (J) | 88.62 | $6.17 \times 10^{-15}$ | $3.57 \times 10^{10}$ | $4.81 \times 10^{-7}$ | $2.45 \times 10^{-10}$ | $3.22 \times 10^{9}$ | 9.02 |

Note:
$P_w$ = Average number of protein molecules per liposome

TABLE 3

PROTEUS VULGARIS

| VET Sample | COMPOSITION (mg) | | $d_w$ (nm) | Moles Lipid per ml |
|---|---|---|---|---|
| | DPPC | PI | | |
| (K) | 27 | 1 | 98.16 | $3.79 \times 10^{-6}$ |
| (L) | 27 | 2 | 70.48 | $3.91 \times 10^{-6}$ |
| (M) | 27 | 3 | 80.44 | $5.03 \times 10^{-6}$ |
| (N) | 27 | 4 | 86.03 | $1.38 \times 10^{-6}$ |
| (P) | 27 | 5 | 92.2 | $1.42 \times 10^{-6}$ |
| (Q) | 27 | 6 | 82.69 | $1.46 \times 10^{-6}$ |

| | $d_w$ | Projected Area m$^2$ | No. of liposomes at monolayer coverage | Moles lipid added to plate | Moles lipid adsorbed to plate | No. of adsorbed vesicles | % Targeted vesicles |
|---|---|---|---|---|---|---|---|
| (K) | 98.16 | $7.57 \times 10^{-15}$ | $2.91 \times 10^{10}$ | $7.58 \times 10^{-7}$ | $1.95 \times 10^{-10}$ | $1.13 \times 10^{9}$ | 3.88 |
| (L) | 70.48 | $3.90 \times 10^{-15}$ | $5.65 \times 10^{10}$ | $7.82 \times 10^{-7}$ | $1.85 \times 10^{-10}$ | $2.20 \times 10^{10}$ | 38.92 |
| (M) | 80.44 | $5.08 \times 10^{-15}$ | $4.33 \times 10^{10}$ | $1.00 \times 10^{-6}$ | $3.67 \times 10^{-9}$ | $3.27 \times 10^{10}$ | 75.50 |
| (N) | 86.03 | $5.81 \times 10^{-15}$ | $3.79 \times 10^{10}$ | $8.28 \times 10^{-7}$ | $1.399 \times 10^{-9}$ | $1.077 \times 10^{10}$ | 28.4 |
| (P) | 92.2 | $6.67 \times 10^{-15}$ | $3.30 \times 10^{10}$ | $2.84 \times 10^{-7}$ | $4.20 \times 10^{-9}$ | $3.91 \times 10^{10}$ | 84.5 |
| (Q) | 82.69 | $5.37 \times 10^{-15}$ | $4.10 \times 10^{10}$ | $8.75 \times 10^{-7}$ | $4.91 \times 10^{-10}$ | $4.12 \times 10^{9}$ | 10.05 |

TABLE 4

CORYNEFORM HOFAMANNI
(with Con A as targeting species)

| VET Sample | COMPOSITION (mg) | | | $d_w$ (nm) | $P_w$ | Moles Lipid per ml |
|---|---|---|---|---|---|---|
| | DPPC | PI | PEMBS | | | |
| (R) | 27 | 3 | 0 | 76.14 | 0 | $4.03 \times 10^{-6}$ |
| (S) | 27 | 3 | 3 | 86.06 | 6.6 | $4.93 \times 10^{-6}$ |
| (T) | 27 | 3 | 3 | 78.38 | 5.4 | $6.03 \times 10^{-6}$ |

| | $d_w$ | Projected Area m$^2$ | No. of liposomes at monolayer coverage | Moles lipid added to plate | Moles lipid adsorbed to plate | No. of adsorbed vesicles | % Targeted vesicles |
|---|---|---|---|---|---|---|---|
| (R) | 76.14 | $4.55 \times 10^{-15}$ | $4.84 \times 10^{10}$ | $8.06 \times 10^{-7}$ | $4.10 \times 10^{-10}$ | $4.12 \times 10^{9}$ | 8.51 |
| (S) | 86.06 | $5.82 \times 10^{-15}$ | $3.78 \times 10^{10}$ | $9.86 \times 10^{-7}$ | $6.58 \times 10^{-10}$ | $5.06 \times 10^{9}$ | 13.38 |
| (T) | 78.38 | $4.83 \times 10^{-15}$ | $4.56 \times 10^{10}$ | $1.21 \times 10^{-6}$ | $6.61 \times 10^{-10}$ | $6.23 \times 10^{9}$ | 13.66 |

TABLE 5

STAPHYLOCOCCUS EPIDERMIDIS
(DPPG as targeting species)

| VET Sample | Mole % DPPC in DPPC | % Apparent Monolayer Coverage |
|---|---|---|
| (U) | 1.79 | 56.0 |
| (V) | 3.52 | 99.4 |
| (W) | 6.78 | 111.50 |
| (X) | 9.88 | 87.70 |
| (Y) | 12.73 | 74.20 |
| (Z) | 15.43 | 32.30 |

Liposomal lipid concentration was 1.34 ± 0.08 mM.
$d_w$ = 86.6 nm.

TABLE 6

STAPHYLOCOCCUS EPIDERMIDIS

| | COMPOSITION (mg) | | | $d_w$ | Moles Lipid |
|---|---|---|---|---|---|
| | DPPG | PI | Triclosan | (nm) | per ml |
| Initial VETs | 27 | 4 | 0.006 | 92.0 | $1.41 \times 10^{-5}$ |
| VETs Fraction 11 | | | | 101.1 | $2.86 \times 10^{-6}$ |
| VETs Fraction 12 | | | | 94.1 | $9.68 \times 10^{-6}$ |

REGROWTH ASSAY
2 Minute Exposure Time

| | $d_w$ (nm) | Moles Lipid per ml | μg Triclosan per ml | % Kill |
|---|---|---|---|---|
| VETs Fraction 11 | 101.1 | $2.86 \times 10^{-6}$ | 0.702 | 64.4 |
| Free Triclosan | — | — | 0.702 | 47.1 |
| VETs Fraction 12 | 94.1 | $9.68 \times 10^{-6}$ | 0.225 | 54.9 |
| Free Triclosan | — | — | 0.225 | 40.4 |

Free Triclosan and VET samples contained 10% Ethanol

TABLE 7A

STAPHYLOCOCCUS EPIDERMIDIS
(with Phosphatidyl Inositol as Targetting Species)

| | COMPOSITION (mg) | | | $d_w$ | Moles Lipid |
|---|---|---|---|---|---|
| | DPPC | PI | Triclosan | (nm) | per ml |
| Initial VETs | 27 | 4 | 0.006 | 92.7 | $1.38 \times 10^{-5}$ |
| VETs Fraction 11 | | | | 91.5 | $5.10 \times 10^{-6}$ |
| VETs Fraction 12 | | | | 88.6 | $4.60 \times 10^{-6}$ |

REGROWTH ASSAY
2 minute exposure time

| | $d_w$ | Moles Lipid Per ml | μg Triclosan Per ml | % Kill |
|---|---|---|---|---|
| VETs Fraction 11 | 91.5 | $5.10 \times 10^{-6}$ | 0.497 | 20.7 |
| Free Triclosan | — | — | 0.497 | 14.3 |
| VETs Fraction 12 | 88.6 | $4.60 \times 10^{-6}$ | 0.283 | 21.9 |
| Free Triclosan | — | — | 0.283 | 15.8 |

Free Triclosan and VET samples contained 10% Ethanol.

TABLE 7B

STAPHYLOCOCCUS EPIDERMIDIS
(with Phosphatidyl Inositol as Targetting Species)

| | COMPOSITION (mg) | | | $d_w$ | Moles Lipid |
|---|---|---|---|---|---|
| | DPPC | PI | Triclosan | (min) | per ml |
| Initial VETs | 27 | 4 | 0.006 | 91.4 | $1.38 \times 10^{-5}$ |
| VETs Fraction 11 | | | | 87.7 | $4.83 \times 10^{-6}$ |
| VETs Fraction 12 | | | | 83.9 | $4.96 \times 10^{-6}$ |

REGROWTH ASSAY
2 minute exposure time

| | $d_w$ | Moles Lipid Per ml | μg Triclosan Per ml | % Kill |
|---|---|---|---|---|
| VETs Fraction 11 | 87.7 | $4.83 \times 10^{-6}$ | 0.451 | 18.4 |
| Free Triclosan | — | — | 0.451 | 8.9 |
| VETs Fraction 12 | 83.9 | $4.96 \times 10^{-6}$ | 0.433 | 18.4 |
| Free Triclosan | — | — | 0.433 | 8.8 |

Free Triclosan and VET samples contained 10% Ethanol.

What is claimed is:

1. A cosmetic composition for topical application to skin and/or hair comprising: particles which include a cosmetically effective benefit agent, said particles having means to bind to an organic surface at a target location accessible on application of the composition to the skin and/or hair; and, optionally, a cosmetically acceptable vehicle, said means to bind comprising at least one antibody or antibody fragment carried by the particles at their surfaces, wherein said antibody or antibody fragment binds to a target site on the skin and/or hair.

2. A composition according to claim 1 wherein the particles are microcapsules which enclose the benefit agent.

3. A composition according to claim 1 wherein the particles are liposomes which enclose the benefit agent.

4. A composition according to claim 3 wherein said liposomes comprise surface active molecules including at least one compound selected from glycolipids and phospholipids having sugar or polyhydric alcohol head groups, said at least one glycolipid or phospholipid being effective to promote binding of the liposomes at the target location.

5. A composition according to claim 4 wherein said at least one glycolipid or phospholipid accounts for from 6 to 18 mole % of the surface active molecules of the liposomes.

6. A composition according to claim 1 wherein the antibody or antibody fragment has affinity for an organic surface at a target site selected from skin, hair, hair follicles, sweat ducts, scalp, feet, underarm and skin lesions.

7. A composition according to claim 1 wherein the antibody or antibody fragment means has affinity for a microorganism present at the target location.

8. A composition according to claim 7 wherein the microorganism is selected from the genera Pityrosporum, Malassezia, Coryneform, Propionibacterium, Micrococcus, Staphylococcus, Proteus and Trichophyton.

9. A composition according to claim 1 wherein the benefit agent is selected from antimicrobials, anti-inflammatory agents, hair growth agents, perfumes, anti-perspirants, deodorants, sunscreens, antioxidants, moisturising agents, cleansing agents and conditioning agents.

10. A method of cosmetic treatment of skin and/or hair comprising topically applying to the skin and/or hair a cosmetic composition, said cosmetic composition comprising particles which include a cosmetically effective benefit agent, said particles having means to bind to an organic surface at a target location accessible on application of the composition to the skin and/or hair; and, optionally, a cosmetically acceptable vehicle, said means to bind comprising at least one antibody or antibody fragment carried by the particles at their surfaces, wherein said antibody or antibody fragment binds to a target site on the skin and/or hair.

11. A method for the production of a cosmetic composition according to claim 1 said method comprising:
 including a cosmetically effective benefit agent in particles;
 providing, at the surface of said particles means to bind an organic surface at a target location accessible on application of the composition to the skin and/or hair; and, optionally, admixing said particles and a cosmetically acceptable vehicle; said means to bind comprising at least one antibody or antibody fragment carried by the particles at their surfaces wherein said antibody or antibody fragment binds to a target site on the skin and/or hair.

\* \* \* \* \*